(12) United States Patent
Ott et al.

(10) Patent No.: US 9,433,405 B2
(45) Date of Patent: Sep. 6, 2016

(54) RETRACTOR WITH ADJUSTABLE BLADES

(75) Inventors: Ingo Ott, Darmstadt (DE); Rainer Hermle, Gosheim (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 660 days.

(21) Appl. No.: 12/508,863

(22) Filed: Jul. 24, 2009

(65) Prior Publication Data

US 2010/0022845 A1    Jan. 28, 2010

(30) Foreign Application Priority Data

Jul. 25, 2008  (DE) .................. 10 2008 034 722

(51) Int. Cl.
*A61B 17/02* (2006.01)
*A61B 17/28* (2006.01)

(52) U.S. Cl.
CPC .... *A61B 17/0206* (2013.01); *A61B 2017/2837* (2013.01)

(58) Field of Classification Search
CPC ....................................... A61B 1/32
USPC ............................... 600/213–217
See application file for complete search history.

(56) References Cited

U.S. PATENT DOCUMENTS

| | | | |
|---|---|---|---|
| 3,384,077 A | 5/1968 | Gauthier | |
| 3,384,078 A | 5/1968 | Gauthier | |
| 3,509,873 A * | 5/1970 | Karlin et al. | 600/226 |
| 4,616,635 A * | 10/1986 | Caspar et al. | 600/215 |
| 5,297,538 A | 3/1994 | Daniel | |
| 5,813,978 A | 9/1998 | Jako | |
| 5,993,385 A * | 11/1999 | Johnston et al. | 600/213 |
| 6,042,540 A * | 3/2000 | Johnston et al. | 600/213 |
| 6,139,493 A * | 10/2000 | Koros et al. | 600/215 |
| 8,062,217 B2 * | 11/2011 | Boucher et al. | 600/215 |
| 2005/0080320 A1* | 4/2005 | Lee et al. | 600/214 |
| 2005/0159650 A1* | 7/2005 | Raymond et al. | 600/201 |

(Continued)

FOREIGN PATENT DOCUMENTS

| | | |
|---|---|---|
| DE | 2951664 A1 | 7/1981 |
| DE | 3509787 A1 | 10/1985 |

(Continued)

OTHER PUBLICATIONS

German Search Report; Application No. 10 2008 034 722.1; Apr. 16, 2009; 3 pages.

(Continued)

*Primary Examiner* — Samuel Hanna
(74) *Attorney, Agent, or Firm* — Whitmyer IP Group LLC

(57) ABSTRACT

A retractor with at least two spreader arms that can be displaced relative to one another and can be blocked by a blocking device and on their end sections are provided with blades that can be displaced in their gripping ranges. The blades are of unit construction and are inserted so that they can slide in linear guides forms from spreader arms in such a manner that can be fixed in a range of freely chosen positions each corresponding to various griping ranges by means of a releasable fixing device.

6 Claims, 7 Drawing Sheets

(56) References Cited

U.S. PATENT DOCUMENTS

| | | |
|---|---|---|
| 2006/0063977 A1* | 3/2006 | Sharratt et al. ............... 600/212 |
| 2006/0084843 A1* | 4/2006 | Sommerich et al. ......... 600/210 |
| 2007/0100212 A1* | 5/2007 | Pimenta et al. .............. 600/210 |
| 2007/0156024 A1* | 7/2007 | Frasier et al. ................ 600/219 |
| 2007/0203399 A1* | 8/2007 | Gephart et al. .............. 600/219 |
| 2007/0208227 A1* | 9/2007 | Smith .................... A61B 1/313 600/219 |
| 2008/0021285 A1* | 1/2008 | Drzyzga et al. .............. 600/215 |

FOREIGN PATENT DOCUMENTS

| | | |
|---|---|---|
| DE | 20119971 U1 | 3/2002 |
| FR | 690530 A | 9/1930 |

OTHER PUBLICATIONS

European Search Report & Written Opinion; Application No. EP 09 00 9551; Nov. 6, 2009; 8 pages.

\* cited by examiner

RETRACTOR WITH ADJUSTABLE BLADES

CROSS-REFERENCE TO RELATED APPLICATIONS

The present application claims priority of German patent application No. 10 2008 034 722.1 filed on Jul. 25, 2008.

FIELD OF THE INVENTION

The invention is in the technical area of surgical instruments and relates generically to a retractor having blades that are adjustable within their gripping range.

BACKGROUND OF THE INVENTION

Retractors, also known as wound spreaders, serve to hold open a wound during a surgical procedure and to allow the operator free access to the surgical area.

In a typical mode of construction, retractors comprise two spreader levers ("branches") that are connected to one another in hinged manner and are provided on one side of the hinge with spreader arms for insertion into an incision and on its other side with actuation arms for actuating the retractor. Attached to the spreader arms, as a rule, are flat-shaped spreader elements ("blades"), which can be hooked onto the borders of the incision. The two spreader levers can be pivoted and the blades can be brought to a selectable relative distance by means of a manual actuation of the actuation arms, which are usually equipped with finger insertion loops for this purpose. A releasable catching toothed connection serves to block the spreader lever in the particular spread position.

Retractors of this type are commercially available in considerable number, for instance as the Weitlaner retractor (DI 58249), and have already been copiously described in patent literature.

The disadvantage of retractors, in particular, is the fact that the blades are frequently not replaceable, so that various retractors must be kept in reserve for different uses, depending for instance on the strength of the tissue layer that is to be held back. This involves relatively high manufacturing costs. In addition, in many cases, only when the retractor is inserted in the wound is it possible to know which blades are best suited to hold the wound open. However, because retractors are usually equipped with symmetrically shaped blades, even when a retractor with blades that are basically appropriate in shape and size is inserted into a wound, an unsatisfactory result can occur if opposite sides of a wound are situated at different anatomical heights. In this case a difference in working length is required for the oppositely placed blades.

To solve this problem, German patent No 35 09 787 C2 discloses a surgical instrument for spreading the edges of a wound with blades whose gripping range or working length is adjustable. The blades each consist of two parts that can be slid with respect to one another and that can be moved into different relative positions and fixed there by a spindle mechanism. The gripping areas are displaced by manually rotating the spindle with a screwdriver.

The principal disadvantage of this surgical instrument is the two-part configuration of the blades and their coupling by a spindle mechanism, causing relatively high production costs in industrial mass manufacturing. In addition, the displacement of the working length of the blades can be achieved only with some difficulty by using a screwdriver, sometimes costing no small loss of time in the course of an operation and requiring a helping "third hand." Owing to the use of a tool to adjust the working length of the blades and the possibility of exerting a relatively great force in the process, there is the risk that the blades can be adjusted at too great a length and that tissue can be unintentionally damaged. In addition, blades of this type are difficult to clean, because impurities can easily become lodged, in particular, in the area between the two parts of a blade and in the threads of the spindle mechanism.

Another important disadvantage of this instrument is the fact that the blades are not replaced, so that only the working length of the blades can be adjusted, without any possibility of varying the shape of the blades, in particular the number of prongs.

On the other hand, it is the object of the present invention to make available a surgical retractor by which the cited disadvantages of conventional retractors with blades with adjustable gripping range can be avoided.

SUMMARY OF THE INVENTION

These and other objects are fulfilled according to the proposed invention by a retractor with the characteristics of the independent patent claims. Advantageous configurations of the invention are indicated by the characteristics of the subsidiary claims.

A generic retractor comprises at least two spreader arms that can be displaced with respect to one another. Each of the spreader arms is equipped on their end sections with spreader elements (blades) for engaging in the edges of a wound that have adjustable gripping range and flat-shaped spreader elements (blades).

Here and in the following, the term "gripping range" of a blade is understood to refer to that part of a blade that serves to engage in the edge of a wound and thus extends from the spreader arm to the distal end of the blade, in particular to its prong(s). The gripping range of a blade corresponds to its (effective) working length in the direction of extension.

The inventive retractor is distinguished essentially in that at least one of the blades is of one-piece construction and is held in a linear guide shaped by a spreader arm so that it can be linearly slid in its extension direction in such a way that it can be fixed by choice by means of a releasable fixing device in a number of different positions (at least two) that each correspond to different gripping ranges (that is, different working lengths). According to the invention, then, the working length or the gripping range available for engaging in a wound can advantageously be altered and adjusted to the particular situation, without the need for changing the actual blade length as is the case with the aforementioned adjustable two-part blades.

In a particularly advantageous configuration of the inventive retractor, the linear guide is configured in the form of a dovetail guide open on both sides in the guide direction, so that the blade, at least in a section that is contained in said guide, has a shape that is complementary to it. Dovetail guides have the particular advantage that the blades fitted in them tilt under pressure in such a direction that the affixing of the blades in the guide direction is reinforced by the fixing device.

In another advantageous configuration of the inventive retractor, the releasable fixing device comprises at least one engaging set that includes an engaging means which engages in force-locking or form-locking connection in a corresponding recess. The engaging means is hereby connected with a selected element with a spreader arm and a blade attached to it, and a number of recesses for engaging with the engaging means are shaped on the respective other element. A particularly advantageous result here is a catch mechanism. The engaging means, which is of spherical shape for instance, can be brought into force- and/or form-locking engagement with one of the recesses in each case, which are of circular or spherical configuration for instance. The recesses are advantageously configured on the blades, for instance spaced at equal intervals, in a row along their extension directions.

The engaging means can also take the form of a threaded element, for instance, which in each case can be brought into force- and/or form-locking engagement with one of the recesses.

In a preferred configuration of the inventive retractor, said retractor is equipped with two spreader levers that are connected in hinged manner and each of which comprises a spreader arm on one side of the hinge on which is mounted a blade for engaging in a wound and an actuation arm on the other side of the hinge with finger-insertion loops for actuating the retractor.

In another advantageous embodiment of the inventive retractor, the two spreader arms that can be displaced with respect to one another can be blocked by a blocking device in a displaced position that can be freely selected.

The invention is more closely described hereafter with reference to one embodiment, with references to the appended illustrations. Equivalent elements, or those with equivalent effects, are labeled with identical reference numbers in the illustrations.

DETAILED DESCRIPTION OF THE INVENTION

Figure 1:
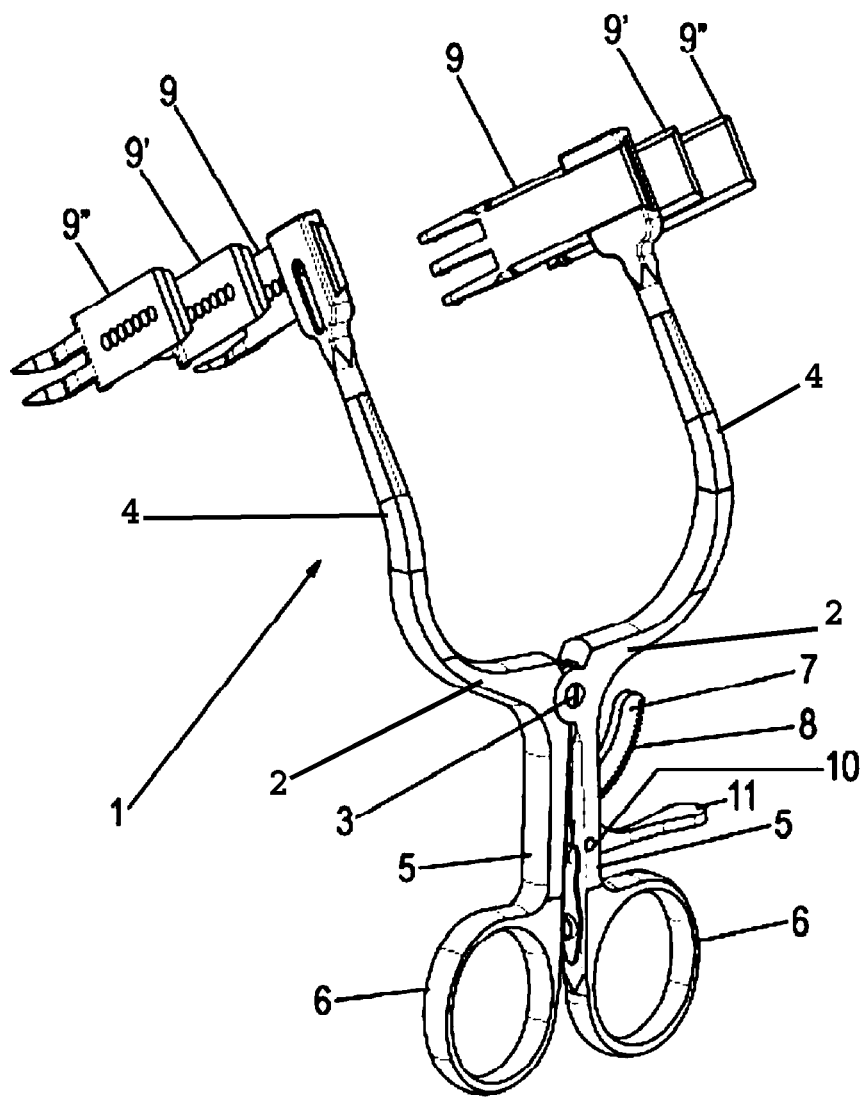
FIG. 1 shows an embodiment of the inventive retractor in perspective view.
Figure 2:
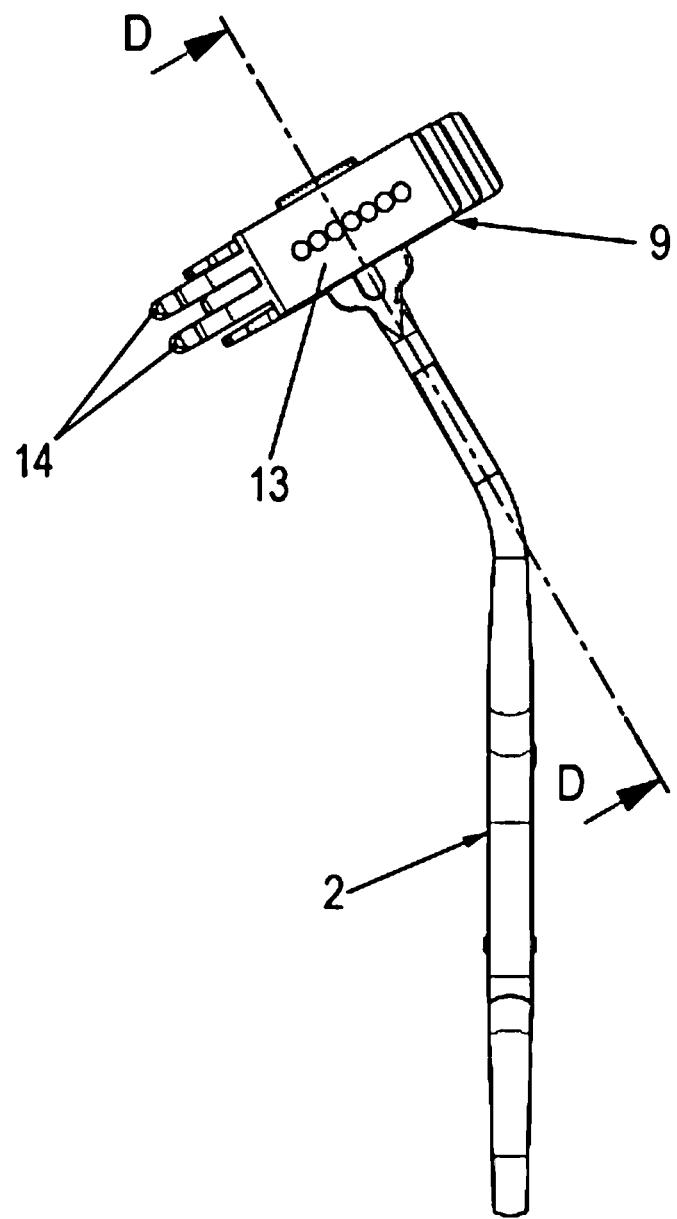
FIG. 2 shows a spreader arm of the retractor from FIG. 1 in another perspective view.
Figure 3:
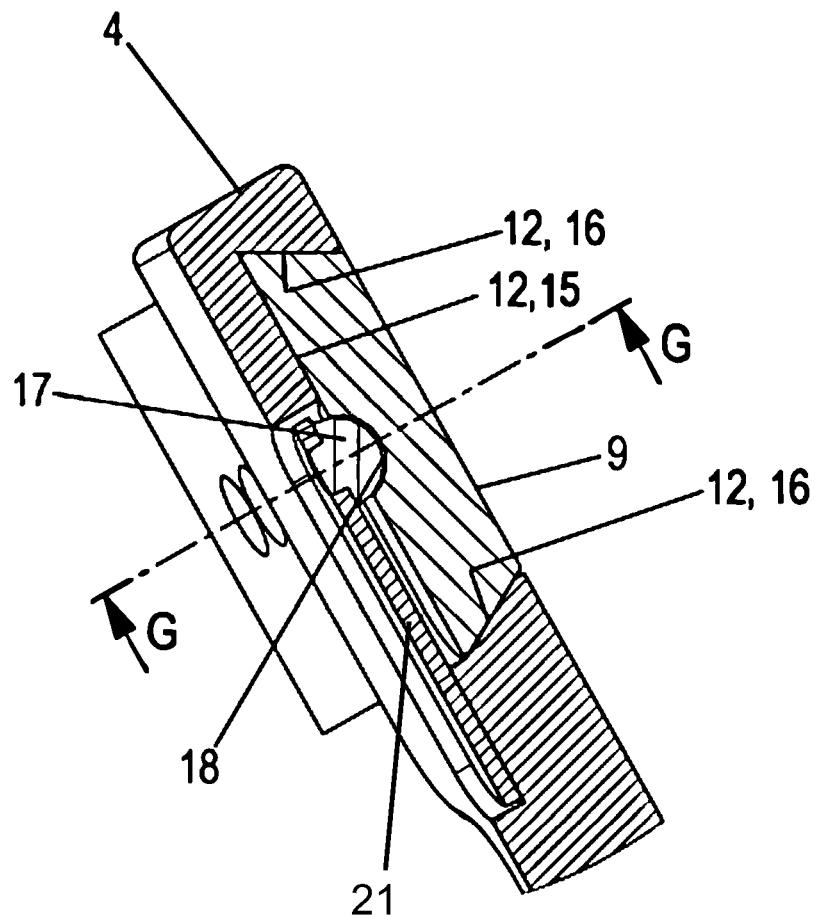
FIG. 3 shows the spreader arm from FIG. 2 along the reference line D-D in a sectional view.
Figure 4:
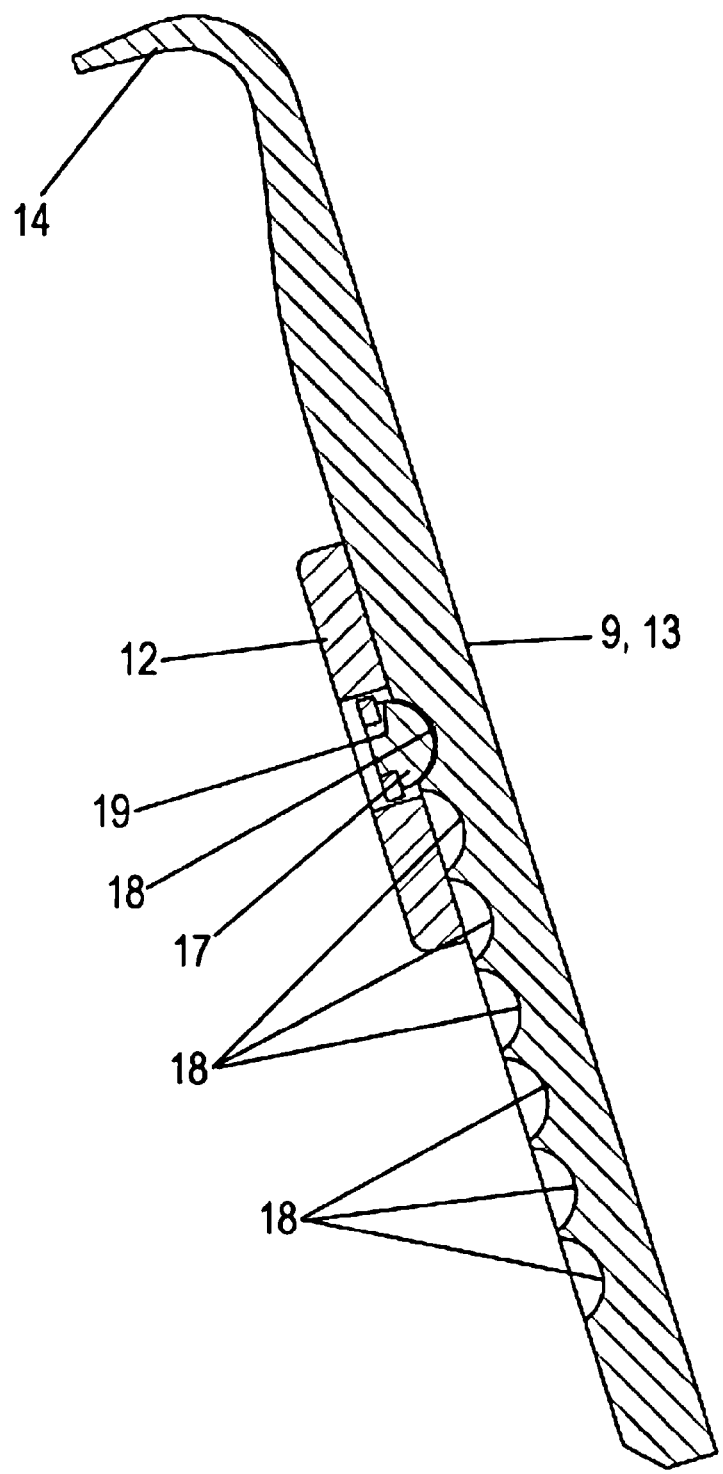
FIG. 4 shows the spreader arm from FIG. 1 along a reference line G-G from FIG. 3 in another sectional view.

With reference to FIGS. 1 through 4, an embodiment of an inventive retractor is hereby described, labeled with the overall reference number 1.

The retractor 1 accordingly comprises two spreader levers 2, which are connected to one another in hinged manner by a hinged connection 3 approximately at their center point. Each of the two spreader levers 2 includes a spreader arm 4 positioned on the one side of the hinged connection 3 and an actuation arm 5 positioned on the other side of the hinged connection 3. The end portions of the two actuation arms 5 are each provided with finger insertion loops 6 serving to move the spreader levers 2 manually and to bring the spreader arms 4 into various pivoting or spreading positions.

By means of a blocking device configured in the form of a catch toothed connection, the spreader levers 2 can be latched in a freely selected pivot position in which the two blades 9 assume a desired relative distance from one another. The catch toothed connection includes an arch-shaped tongue that is positioned on one of the two actuation arms and having a toothed connector 8 running along the arch and a kink or loop (covered in FIG. 1) that is held in engagement with the toothed connection by a spring 20. The kink is shaped by a finger lever 11, which is connected to the other actuation arm by means of a hinged pin 10. The teeth of the toothed connection 8 are shaped in such a way that the kink can glide over the toothed connection 8 in the manner of a ratchet mechanism upon bringing together the two finger insertion loops 6, but is hooked in the tooth gaps in the reverse motion direction and thus blocks the spreader arms 4 from being brought together. By actuating the finger lever 11 against the spring force of the spring holding the kink in engagement with the toothed connection 8, the catching mechanism can be released in order to move the two spreader arms 4 toward one another.

One-piece blades 9 are positioned on the end sections of the two spreader arms 4 to engage in the facing edges of the wound. The blades 9 each consist of a flat surface section 13 and bent prongs 14 at a distance from the surface section 13 in the direction of extension of the blades 9. The blades 9 are mounted on the end sections of the two spreader arms 4 so that they can slide in the extension direction and for this purpose are each inserted with their flat section 13 in a dovetail guide 12 shaped to the end sections of the spreader arms 4. Each dovetail guide 12 is shaped in the manner of a dovetail perpendicular to the extension direction of the blades 9; that is, each comprises a base surface 15 shaped approximately flush to the extension direction of the end section of the related spreader arm 4, and two conically converging side surfaces 16 that are placed at an acute angle (an angle less than 90 degrees) to the base surface 15 and surround the inserted blades 9 on three sides. The two dovetail guides 12 are consequently positioned in such a way that they each taper conically toward the other dovetail guide 12. The blades 9 in the area of the surface section 13 comprise a complementary fitting shape to the dovetail guide 12, so that the surface sections 13 are contiguous with the base surface 15. The dovetail guides 12 make possible a linear displacement of the blades 9 along their extension directions and hold the blades 9 firmly in the other directions.

The blades 9 are each fixed in place by a spring loaded catch mechanism, which comprises a catching sphere 17 that is inserted inside the dovetail guide 12 in a spherical recess 19 and which is brought into engagement with a recess 18 of the blade 9 shaped in the surface section 13 via a spring means 21. The surface sections 13 of each blade 9 are each provided for this purpose with a number of recesses 18 that are positioned at approximately equal distances in the extension direction of the blade 9. The spherical-bowl-shaped recesses 18 include a corresponding adjusted shape to the catching sphere 17. The catching sphere 17 and a recess 18 located in engagement with the catching sphere 17 together form an engaging pair.

Because of the catch mechanism, each blade 9 can be fixed in various catch positions corresponding to the particular engaging pair that are in engaged position along their extension direction within the dovetail guide 12. By changing the catch position here, it is possible to adjust the gripping range or working length of a blade 9, which is determined by the distance of the distal end of the blade 9 (or of its prongs 14) from the related spreader arm 4. The blades 9 can extend out of the dovetail guide 12 in catch positions with a gripping range that is shortened with respect to the maximum gripping range because of the dovetail guides 12 that are open on both sides in the extension direction. The blades are displaced manually inside the dovetail guides 12, so that the catch mechanisms on the one hand ensures a good slidable ability and on the other hand a more secure stationary position. With the retractor 1 brought into working position, a force is exerted on the blades 9 by the wound edges so that the blades are pressured in the direction toward one another. This results, in particularly advantageous manner, to a tilting of the blades 9 in the dovetail guides 12, so that the securing of the blades 9 is reinforced.

In the illustrations the blades 9 are provided by way of example with seven recesses 18 (correspond to seven different catch stages) positioned each at an equal interval in a row along the sliding or extension direction of the blades 9. It should be mentioned for the sake of completeness that a greater or smaller number of catch stages is also possible.

Another possibility would be that instead of a spring-loaded catch sphere 17, a manually movable screw is provided, which can be brought each time into force-locking and/or form-locking engagement with the recesses 18 formed in the flat section 13.

Figure 5:
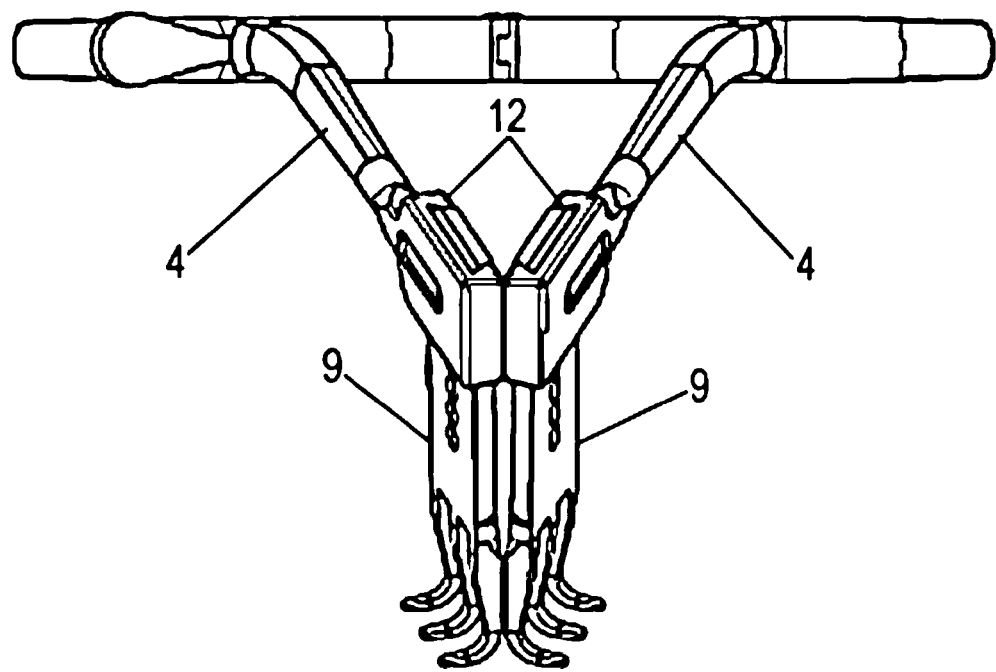
FIG. 5 shows in another perspective view the retractor from FIG. 1 with closed spreader arms.
Figure 6:
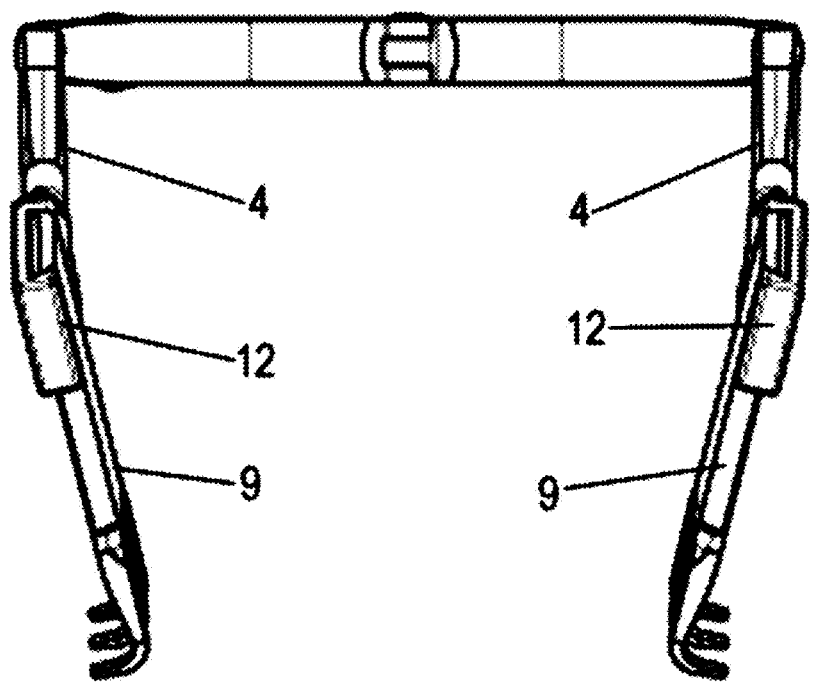
FIG. 6 shows in another perspective view the retractor from FIG. 1 with opened spreader arms and blades with maximum gripping range.
Figure 7:
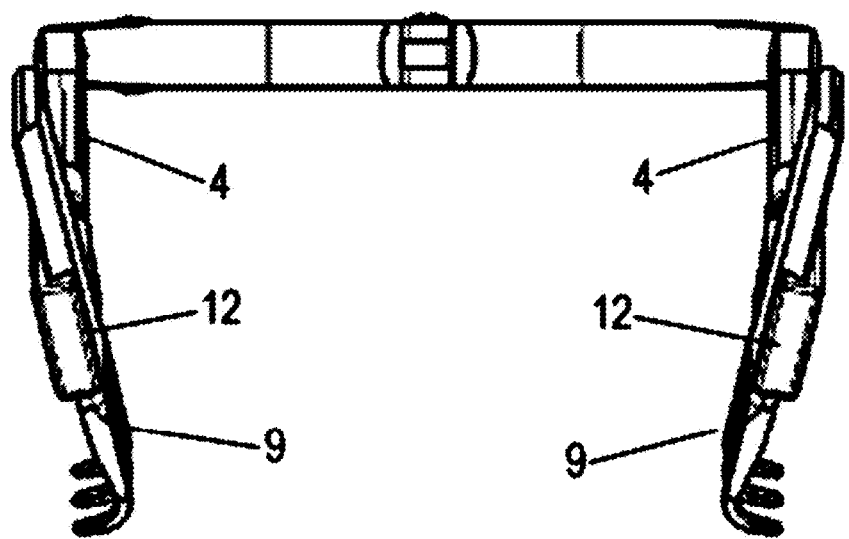
FIG. 7 shows in another perspective view the retractor from FIG. 1 with opened spreader arms and blades with minimum gripping range.

FIGS. 5 through 7 show various positions of the two spreader levers 2. FIG. 5 shows a situation in which the two spreader arms 4 touch one another, corresponding to a maximum distance of the two finger engagement loops 6. In FIG. 6 the two spreader arms 4 are brought into a maximum spread position by joining together the finger engagement loops 6. The minimally employed blades (9) in the extension direction have here a maximum working length (maximum gripping range), that is, the catching sphere 17 engages in that recess 18 that is farthest away from the prongs 14. On the other hand, FIG. 7 depicts a situation in which the two blades 9 have a minimum working length (minimum gripping range), that is, the catching sphere 17 engages in that recess 18 that is the least distant from the prongs 14. Corresponding to the various catching stages, the working length of the one-piece blades 9 can be varied between the minimum and maximum working length. Although this is not shown in the figures, it is also possible to select at will from differing working lengths for the two blades 9, in particular to insert the retractor 1 in wounds with wound edges at various anatomical heights.

On the basis of the dovetail guides 12 open on both sides in guide direction, the blades 9 can very easily be replaced in order to employ blades of various sizes or shapes depending on the purpose of the application. For instance, in FIG. 1 additional blades 9', 9" are shown that differ from one another in the number of their prongs.

The invention claimed is:

1. A retractor comprising:
two spreader levers hingedly connected to one another by a hinge, each of the two spreader levers having one spreader arm and one proximal actuation arm positioned on opposite sides of the hinge, the spreader arms of said two spreader levers are rotatable relative to one another about said hinge in a desired spread position, each actuation arm of said actuation arms having a finger-insertion loop for actuating the retractor, each spreader arm of said spreader arms having a distal end section which extends longitudinally in a first direction away from said hinge, wherein for each spreader lever, the respective actuation arm, the respective spreader arm and the respective end section are monolithic;
a linear guide formed in each of said distal end sections of said two spreader arms, said linear guide being a channel formed in the respective distal end section to slidably receive a blade, the entire linear guide extending only between top and bottom sides of the respective distal end section and in a second direction that is perpendicular to the first direction;
a plurality of blades configured to be slidably received in the channels of the linear guides and are adjustable in a gripping range within the linear guides of the end sections for engaging in a wound;
said channel of each linear guide is configured in the form of a dovetail guide open on opposite sides of the linear guide and the plurality of blades each comprises a complementary form-fitting profile for the dovetail guide open on opposite sides of the linear guide;
each of the plurality of blades is of one-piece unitary construction;
wherein one blade of the plurality of blades is insertable into one of said channels of said linear guides and is slidable in the respective channel of the linear guide in a direction of extension along the second direction in such a way that said one blade is fixed by free choice in one of a number of different axial positions along the respective linear guide by a releasable fixing device, said number of different axial positions correspond to said gripping range; and
wherein the releasable fixing device has at least one engaging pair that includes a spring-loaded detent disposed within said respective channel of said respective linear guide at a location between top and bottom sides of said respective spreader arm and a plurality of recesses on said one blade, said spring-loaded detent being configured to interlock with one of said plurality of recesses to selectively adjust displacement of said one blade within said respective linear guide relative to said respective distal end section.

2. The retractor according to claim 1, wherein the spring-loaded detent grips by one of force-locking and form-locking connection into one of the plurality of recesses.

3. The retractor according to claim 2, wherein the releasable fixing device forms a catch mechanism.

4. The retractor according to claim 3, wherein the spring-loaded detent is spherical in shape and each of the plurality of recesses is of circular or spherical configuration.

5. The retractor according to claim 2, wherein the plurality of recesses are positioned on said one blade in a row along the direction of extension.

6. The retractor according to claim 1, wherein a releasable blocking device is adapted to block the spreader levers in the desired spread position.

* * * * *